United States Patent
Noe et al.

(10) Patent No.: US 11,266,600 B2
(45) Date of Patent: Mar. 8, 2022

(54) EMULSIONS FOR THE TOPICAL TREATMENT OF DERMAL AND MUCOSAL INFECTIONS

(71) Applicant: ProFem GmbH, Vienna (AT)

(72) Inventors: Marion Noe, Vienna (AT); Christian R. Noe, Vienna (AT)

(73) Assignee: ProFem GmbH, Vienna (AT)

( * ) Notice: Subject to any disclaimer, the term of this patent is extended or adjusted under 35 U.S.C. 154(b) by 0 days.

(21) Appl. No.: 16/763,395

(22) PCT Filed: Nov. 14, 2018

(86) PCT No.: PCT/EP2018/081264
§ 371 (c)(1),
(2) Date: May 12, 2020

(87) PCT Pub. No.: WO2019/096863
PCT Pub. Date: May 23, 2019

(65) Prior Publication Data
US 2020/0281853 A1    Sep. 10, 2020

(30) Foreign Application Priority Data

Nov. 14, 2017 (EP) .................................... 17201650
Nov. 14, 2017 (EP) .................................... 17201651

(51) Int. Cl.
| | | |
|---|---|---|
| *A61K 9/107* | (2006.01) | |
| *A61P 15/02* | (2006.01) | |
| *A61P 31/04* | (2006.01) | |
| *A61K 31/196* | (2006.01) | |
| *A61K 9/10* | (2006.01) | |
| *A61K 31/4174* | (2006.01) | |
| *A61K 47/22* | (2006.01) | |
| *A61K 9/00* | (2006.01) | |
| *A61K 9/06* | (2006.01) | |
| *A61K 45/06* | (2006.01) | |

(52) U.S. Cl.
CPC ............... *A61K 9/107* (2013.01); *A61K 9/10* (2013.01); *A61K 31/196* (2013.01); *A61K 31/4174* (2013.01); *A61K 47/22* (2013.01); *A61P 15/02* (2018.01); *A61P 31/04* (2018.01); *A61K 9/0014* (2013.01); *A61K 9/0034* (2013.01); *A61K 9/06* (2013.01); *A61K 45/06* (2013.01)

(58) Field of Classification Search
CPC ...... A61K 9/107; A61K 9/10; A61K 31/4174; A61K 47/22; A61K 31/196; A61K 9/0034; A61K 9/0014; A61K 9/06; A61K 45/06; A61K 31/085; A61K 47/10; A61K 47/186; A61K 31/14; A61K 31/192; A61K 31/4706; A61K 31/496; A61K 31/665; A61K 31/7056; A61K 2300/00; A61K 31/4164; A61K 31/205; A61P 15/02; A61P 31/04; A61P 31/10; A61P 29/00; Y02A 50/30; A61Q 7/00
See application file for complete search history.

(56) References Cited

U.S. PATENT DOCUMENTS

| | | |
|---|---|---|
| 5,686,089 A | 11/1997 | Mitra et al. |
| 2004/0101538 A1 | 5/2004 | Larnier et al. |
| 2007/0292355 A1 | 12/2007 | Tamarkin et al. |
| 2009/0208558 A1 | 8/2009 | Noe et al. |
| 2011/0159104 A1 | 6/2011 | Teslenko |
| 2011/0281809 A1 | 11/2011 | Campbell et al. |
| 2014/0030312 A1 | 1/2014 | Noe et al. |
| 2016/0120797 A1* | 5/2016 | Rayudu .............. A61K 31/7056 424/450 |
| 2019/0022000 A1 | 1/2019 | Tamarkin et al. |

FOREIGN PATENT DOCUMENTS

| | | |
|---|---|---|
| AT | 11 910 U1 | 7/2011 |
| CL | 199900408 | 10/1999 |
| CL | 201201227 | 8/2012 |
| CL | 292001272 | 10/2020 |
| DE | 10 2008 034 944 A1 | 1/2010 |
| EP | 0 923 937 A2 | 6/1999 |
| WO | WO 02/078648 A2 | 10/2002 |
| WO | WO 2007/131253 A2 | 11/2007 |
| WO | WO 2011/060083 A1 | 5/2011 |

OTHER PUBLICATIONS

International Search Report dated Feb. 12, 2019 in PCT/EP2018/081264 filed on Nov. 14, 2018, 4 pages.
European Search Report and Written Opinion dated May 29, 2018 in European Application No. 17201650.3, 14 pages (with English Translation of Category of Cited Documents).
European Search Report and Written Opinion dated Jun. 1, 2018 in European Application No. 17201651.1, 14 pages (with English Translation of Category of Cited Documents).
Mendling, W. et al., "Use of locally delivered dequalinium chloride in the treatment of vaginal infections: a review," Arch Gynecol Obstet, vol. 293, 2016, pp. 469-484, XP035879005.
Combined Chilean Office Action and Search Report dated Aug. 12, 2021 in Chilean Patent Application No. 202001273 (with English translation). 19 pages.

* cited by examiner

*Primary Examiner* — Quanglong N Truong
(74) *Attorney, Agent, or Firm* — Oblon, McClelland, Maier & Neustadt, L.L.P.

(57) ABSTRACT

The invention relates to an emulsion for the topical treatment of dermal infections and mucosal infections, in particular of urogenital infectious diseases, characterized in that an antimicrobial agent and an anti-adhesive agent, preferably an NSAID, are used in combination.

25 Claims, No Drawings

EMULSIONS FOR THE TOPICAL TREATMENT OF DERMAL AND MUCOSAL INFECTIONS

The invention relates to emulsions for the topical treatment of dermal infections and mucosal infections, in particular urogenital infections.

Man lives in symbiosis with a gigantic number of microorganisms, which mainly colonise his intestines and skin surface as commensals. The totality of these microorganisms is called the human microbiome. The microbiome of the female vagina, in which lactic acid bacteria predominate, has a very special composition. Under normal physiological conditions, these bacteria create a weakly acidic environment in the vagina which has a protective effect against bacterial infections. Nevertheless, vaginal infections frequently occur for various reasons, caused on the one hand by the almost ubiquitously present fungi of the species *Candida*, which easily change from commensals to pathogens, and on the other hand by bacteria such as *Gardnerella vaginalis, Mobiluncus* or *Prevotella* spp, and by streptococci or staphylococci or for example by typical intestinal germs such as *Enterobacter, E. coli* and/or for example *Klebsiella pneumoniae*, which can easily enter the vagina by infection as a result of smearing due to the proximity of the body orifices. Initially, asymptomatic miscolonisation is the result. If certain threshold values of foreign germs are exceeded and infection-supporting factors are added, a virulent infectious event ultimately breaks out. If this is not treated in time, the infection can become chronic, usually with biofilm formation. Even asymptomatic miscolonisation is being recognised increasingly as a risk factor for infertility, miscarriage and premature birth, but also for cystitis and certain forms of incontinence.

US 2007/292355 A1 relates to anti-infective foamable compositions containing an anti-infective and a keratolytic agent. The compositions are used in the treatment of fungal, bacterial or viral infections.

AT 11 910 U1 relates to a composition comprising chlorhexidine, bisphosphonate, a non-steroidal anti-inflammatory drug (NSAID) and an immunomodulator (tetracycline) for the treatment or prevention of, inter alia, oral, mucosal or dermal infections or inflammation.

DE 10 2008 034944 A1 relates to honey-based microemulsions which, together with other active substances, including NSAIDs inter alia, can be introduced into the body by topical application to the skin or orally, nasally or percutaneously.

The WO 2011/060083 A1 relates to methods for the prevention or treatment of external ear inflammation with compositions containing antibiotics, antimycotics, antiparasitics, antiviral active substances, NSAIDs, analgesics, anaesthetics and/or steroids.

WO 02/078648 A2 relates to topical pharmaceutical compositions containing an antimycotic, for example terbinafine, and a further drug, for example diclofenac or indomethacin.

The present invention relates to medicaments for the topical treatment of bacterial dysbioses and manifest infectious diseases, including mixed infections with fungi and other microorganisms. Accordingly, the present invention relates to an emulsion for the topical treatment of dermal infections and mucosal infections, in particular of urogenital infectious diseases, in particular for use in the topical treatment of urogenital bacterial infections, which is characterised in that an antimicrobial active substance and an anti-adhesive active substance, preferably an NSAID, are used in combination.

Bacterial miscolonisation of the vagina and even symptomatic vaginal infections are frequent. The transition from asymptomatic, not yet inflammatory miscolonisation to symptomatic illness is defined more precisely by the terms vaginosis and vaginitis. The terms aerobic vaginose/vaginitis and anaerobic vaginose/vaginitis (syn.: bacterial vaginosis) represent a more precise definition of the causative pathogens. A problem common to all vaginal infections, regardless of the pathogen organism, is the formation of what are known as biofilms. The mucosal surfaces of the affected organs (vagina, urethra, bladder, penis) are covered by these biofilms. In these biofilms, the microorganisms are surrounded by a layer of mucus substances. The individual microbial components of the biofilm take over different tasks in the cell system and also exchange resistance mechanisms. The germs most frequently found in bacterial dysvaginosis are above-average biofilm formers. This makes therapeutic access in the case of a manifest infection massively more difficult, and chronification or frequent relapses in the course of the infection are the result. Recent studies confirm that re-infection is often caused by the partner. Partner treatment is therefore always indicated. In men, the germ reservoirs are mostly found in the fold of the foreskin and/or in the first third of the urethra.

Bacterial dysbioses and infections can be efficiently treated by a medicament combination consisting of an antimicrobial drug with an anti-adhesive active substance. By inhibiting adhesion, the biofilm is broken up and detached from the epithelium of the host. This simultaneously releases all the germs contained therein and makes them accessible again for direct antimicrobial treatment. A class of anti-adhesive active substances that is particularly useful is constituted by the non-steroidal anti-inflammatory drugs (NSAIDs). In addition to the anti-adhesive effect, these have an anti-inflammatory effect and immediate pain inhibition, which is a further particular advantage in view of the vaginal infections that are often associated with pain. Since chronic infections are also accompanied by chronic inflammation, the anti-inflammatory effect is also of particular importance, especially in the case of chronic infections. The presence of the NSAID in the described concentrations and conditions in an emulsion in the described composition and in the described proportions is decisive for breaking up the biofilm. NSAIDs which are particularly suitable in the sense of the invention are diclofenac, bufexamac, ibuprofen, dexibuprofen, flurbiprofen, ketoprofen, piroxicam, meloxicam, lornoxicam, flufenamic acid, mefenamic acid, indometacin or naproxen.

The standard concentration at which diclofenac is applied topically dermally is in the range of 1 to 2% (10 mg/or 20 mg/g). In the context of the present invention it is preferred that diclofenac is used in an amount of 0.1% to 0.5% (1-5 mg per g cream), preferably from 0.2% to 0.4%. The usual concentration at which ibuprofen is used topically is 5% (50 mg/g cream/gel). In the context of the invention, ibuprofen is used in a preferred amount of 0.5 to 2.5% (5-25 mg per g cream), preferably from 1 to 2%. Further examples of preferred NSAIDs and their preferred amounts ("Concentration according to the invention") can be found in Table A.

TABLE A

Examples of standard and preferred concentrations according to the invention

| Active substance | Individual dose | Daily maximum dose oral/i.v. | Example | Individual dose | Daily maximum dose topical | Example | Concentration according to the invention |
|---|---|---|---|---|---|---|---|
| Diclofenac sodium | 50-75 mg | 150-225 mg | Voltaren 50 mg tablets 75 mg amp. | 40-80 mg | 240 mg | Voltadol pain relief gel 1%, 10 mg/g 2%, 20 mg/g | 0.2-0.5 wt. % |
| Indometacin | 25-75 mg | 50-150 mg | Indocid 25 mg 75 mg ret. | 20-40 mg | 40-80 mg | IndometGel 1%, 10 mg/g | 0.1-0.4 wt. % |
| Naproxen | 250-500 mg | 1000 mg | Naproxen FT 250/500 mg Naproxen Susp. 50 mg/ml | | | | 0.5-2.5 wt. % |
| Ibuprofen | 200-800 mg | 2400 mg | Ibuprofen FT 200/400/800 mg | 100-250 mg | 1000 mg | Ibutrop cream/gel 5%, 5 g/100 g | 0.5-2.5 wt. % |

The following NSAIDs are particularly preferred within the scope of the invention:

| NSAID | Preferred concentration (wt. %) | Preferred individual dose (mg) |
|---|---|---|
| Diclofenac | 0.1-0.5 (preferably 0.2-0.4) | 4 to 8 mg |
| Indometacin | 0.1-0.4 | 2-8 mg |
| Naproxen | 1-5 | 20 to 100 mg |
| Ibuprofen | 0.5-2.5 | 10 to 50 mg |
| Dexibuprofen | 0.25-1.25 | 5 to 25 mg |
| Ketoprofen | 0.25-1.25 | 5 to 25 mg |
| Mefenamic acid | 0.5-4 | 10-40 mg |
| Lornoxicam | 0.02-0.04 | 0.4 to 0.8 mg |

The concentration restriction according to the table applies to the application on open wounds (possible in case of dermal fungal infections) and on mucosas. For application on less inflamed skin, a maximum NSAID concentration up to the standard topical amount is possible.

In a preferred embodiment, the emulsion is available in the form of a salve or cream. Preferably, it is an emulsion with an aqueous phase and an oil phase, containing an antimicrobial active substance and an NSAID, characterised in that (a) the NSAID in the aqueous phase is in a concentration range that corresponds to half to a tenth of the standard concentration used for these active substances in approved dermal formulations, in that (b) the weight ratio of the water phase to the oil phase in this emulsion is between the values 2.0 and 2.7, and in that (c) the pH value of the emulsion is not less than the value 6.5 and not more than 8.5, preferably in the range 7.0 to 8.0, preferably for the treatment of urogenital infectious diseases, in particular for use in the topical treatment of vaginal infections and female cystitis, and for local partner treatment (glans penis, initial third of the urethra).

In particular, the preparations according to the invention show not only optimised pharmacokinetics by attacking directly at the site of infection, but also optimal pharmacodynamics. This not only enables a particularly good efficacy of the antimicrobial active substance, but also significantly improves the interaction with the NSAID by ensuring sufficient efficacy through a low concentration of NSAID without having to accept the side effects (irritation, burning, etc.) that may occur. In practice, this leads to the fact that combinations of antimicrobial drugs and NSAID, which were previously not usable for these reasons relating to side effects, can be made available to patients with the teaching of the present invention and these patients can now be provided with a successful therapy. According to the invention, however, it has been shown that the concentration of the NSAID in the aqueous phase is of decisive importance for an optimal pharmacodynamic effect. The availability of the introduced NSAID is achieved by the interaction of the preparation process, the water/oil ratio and the pH value, which ensures the predominant presence of the NSAID in its salt form.

Semi-solid emulsions (oil-in-water or water-in-oil), preferably in the form of a cream, are particularly well suited to bring the active substances efficiently and in a concentrated form to surfaces with biofilms. The viscosity of the emulsions is strongly determined by the water-to-oil ratio. Surprisingly it has been found that the water-to-oil ratio is of special importance in the formulation of the emulsion. A higher proportion of fat components hinders the development of the efficacy. By contrast, a lower fat proportion leads to a stronger irritating effect.

It is known that finding a dosage form for topical application in the vagina is made difficult by the fact that the medicament can easily leak during application, which makes reliable dosing difficult. In view of the relatively narrow therapeutic window, drugs according to the present invention presuppose, in order to achieve the desired therapeutic effect, that the active substance, above all the NSAID component, remains safely at the site of action. For this reason, the ratio of the oil phase containing the antimycotic to the water phase containing the NSAID in the medicament is within a relatively narrow range. Thus, if the viscosity is further reduced to a greater extent by increasing the proportion of the aqueous phase, an uncontrolled loss through leakage from the vagina can be expected. Liquid emulsions or gels with a high water content or with low viscosity are to be excluded as dosage forms for the vaginal application according to the present invention.

Since chronic infections of the vagina are at the same time associated with chronic inflammation of the vaginal epithelium, in such cases a cure can only be achieved if it is ensured that the NSAID remains in the vagina.

To achieve an optimal therapeutic effect, the water-to-oil ratio should not exceed a value of 2.7. Above this level, the active substance is flushed out too quickly with the vaginal secretion, which means that there is not enough time to exert its adhesion-suppressing effect on the outer layer of the vaginal epithelium to which the pathogen adheres. The active substance, which is washed out very quickly when the water-to-oil ratio is too high, may at best additionally also cause an irritating effect as a side effect.

In the same way as too much water in the emulsion has a negative effect, too much fat should also be avoided. In view of the low concentration in which the NSAID is used, it is of particular importance, in order to achieve the therapeutic effect, that the release of the active substance at the site of action is rapid and not protracted. A slow release, such as from the oily phase, does not guarantee that the required therapeutic concentration is achieved at the site of action. For this reason, the water-to-oil weight ratio in the emulsion should not fall below 2.0. Consequently, the value of the water-to-oil weight ratio of the emulsions according to the invention also has a window between 2.0 and 2.7, preferably between 2.1 and 2.6, even more preferably between 2.2 and 2.55.

It is essential that the NSAIDs are in salt form (or ionic form) in accordance with the invention, both during incorporation and during use. Therefore, their incorporation into the formulation is important. When the NSAID is incorporated in its free form or when it is incorporated as a salt into the oily phase, the therapeutic effect is massively impaired. Whereas the antimycotic is preferably incorporated into the oily phase and is present therein, the method according to the invention therefore generally involves the NSAID being introduced into the aqueous phase before the emulsion is prepared. Alternatively, the solid salt of the NSAID can be incorporated into the (largely) finished emulsion in finely crystalline or micronised form, or as a hydrogel.

A rapid release is ensured if the active substance is present in the aqueous phase of the emulsion, which presupposes that the NSAID is present as a salt. Most NSAIDs are weak acids with a pKa value of 4-5 (diclofenac 4.15, ibuprofen 4.91, mefenamic acid 4.2, indometacin 4.5, naproxen 4.2). Accordingly, they are already present in the weakly acidic environment, partly in free form, and are thus extracted into the oil phase, which may lead to a reduced effect or loss of effect. Since with decreasing pH value the active substance proportion of the NSAID present as free acid increases in the oil phase, a pH value of at least pH=6 is appropriate in order to have a therapeutic effect in the drugs at the active substance concentrations according to the invention. In the case of NSAIDs, however, there may be a decrease in chemical stability in the alkaline environment (in the case of diclofenac from pH 8.00-8.5). It should also be noted that the pH value of an emulsion influences the fundamental physiological compatibility. For this reason, relatively narrow limits are also set with regard to the pH value of the formulation. According to the invention, the (aqueous phase of the emulsion) has a pH value in the range of 6.5 to 8.5, preferably 7-8.

Within the scope of the invention, antibiotics or antiseptics are preferably used as antimicrobial agents.

Among the bacterial microorganisms found in the vaginal biofilms, typical intestinal germs such as *Enterobacter, E. coli, Klebsiella pneumoniae* and Enterococci, but also ureaplasmas and mycoplasmas, as well as *Gardnerella vaginalis, Prevotella* spp. and *Mobiluncus* play a particular role. Preferred antibiotics within the scope of the present invention which are also particularly suitable for the treatment of these germs are phosphomycin, clindamycin, metronidazole, nitrofurantoin, nitrofurazone, nitrofurantoin, nifuratel, nifuroxacin, nitroxolin, trimethoprim, sulfadiazine and cotrimoxazole.

Antiseptics can act both on non-bacterial microorganisms such as trichomonads as well as on bacteria. At higher concentrations, antiseptics exert an antibacterial effect and are suitable, alone or together with an antibiotic, for combination with an antiadhesive active substance according to the invention. The antimicrobial effect of the antiseptics is mainly based on the disturbance of the integrity of the plasma membrane. Due to the fundamentally identical structure of the membrane of the endothelial cells, these active substance have an inherent potential to induce inflammation. Since this potential is suppressed by NSAIDs, the combination preparations according to the invention of antiseptics offer a very special therapeutic advantage.

Preferred antiseptics are quaternary ammonium salts, such as benzalkonium chloride, and dequalinium chloride, as well as phenoxyethanol. Preferred concentrations are at least 0.2 weight percent for benzalkonium chloride, at least 0.2 weight percent for dequalinium chloride, and at least 2 weight percent for phenoxyethanol. In the context of the present invention, the terms "antimicrobial active substance", "antibacterial active substance", "antibiotics", "antiseptics", etc. shall be understood to mean substances which are regarded as such active substances in normal pharmaceutical use. Which substances are regarded as such active substances can be taken, for example, from the Rote Liste ("Red Data Book") (Rote Liste Service GmbH (editor and publisher), Rote Liste 2014—
Arzneimittelverzeichnis für Deutschland ("Red Data Book 2014—Drug Compendium for Germany") (including EU authorisations and certain medical devices), 2047 pages, ISBN 978-3-939192-80-0), the contents of which are hereby included in this application. No antibacterial active substances within the meaning of the invention are benzyl alcohol, ethanol or propanol.

In the combinations described, the composition of the drug combinations according to the invention is particularly suitable for the treatment of even complex chronic vaginal inflammations.

In special applications it is advisable to add an odorous substance to the emulsion. The addition of a terpene to the emulsion, preferably farnesol, which additionally has a biofilm inhibiting effect, is therefore a preferred subject matter of the invention.

The emulsions according to the invention are suitable for application on mucosas, in particular of urogenital infections. Unsuitable for vaginal application are, for example, compositions which have a high content of mucosa-damaging substances, for example ethanol or isopropanol. It is therefore preferred that the emulsion according to the invention does not contain more than 10% ethanol. It is also preferred that the emulsion according to the invention does not contain more than 20% isopropanol. Since keratinised layers do not occur in mucosas, for example in the urogenital area, a keratolytic effect is not desired. For this reason, the strongly acidic, keratinolytic salicylic acid is not an NSAID according to the invention.

Emulsions according to the present invention are also suitable for the treatment of male urogenital mucosal diseases of the glans penis and urethra.

Cystitis is widespread. It is usually caused by bacterial infection. The bladder is difficult to access for topical treatment. However, since the woman's urethra is located in the front entrance to the vagina, the most common route of infection runs from the vagina into the urethra. In addition, in urological and gynaecological practice, symptoms are often seen which can be attributed to an isolated inflammation of the urethra. The vagina thus becomes the primary germ reservoir for urethritis and cystitis. Even if antibiotic treatment of acute cystitis can be supported by the oral administration of anti-adhesive plant extracts which adhere to the bladder wall, the restoration of the vaginal flora, which is usually also affected by the infection, is nevertheless the basic prerequisite for a lasting cure. This can be achieved with the medicaments according to the invention. For this reason, according to the present invention, medicaments are therapeutic agents efficient against cystitis, either alone or in combination with medicaments acting only in the bladder.

Apart from purely bacterial infections, mixed infections with fungi (mainly yeasts of the genus *Candida*) are also common. In WO 2007/131253 A2, medicament combinations for the topical treatment of fungal infections are claimed whose special effect is based on the fact that in addition to the antimycotic active substance, a further active substance is added which prevents the adhesion of the fungus to the epithelium. Some of the mentioned mixed infections can be treated by the combinations claimed in WO 2007/131253 A2. In severe cases of mixed infections, however, it is advisable or necessary not to limit oneself to the treatment of the fungal infection, but to supplement the medicament with an antibacterial active substance in a triple combination.

The antimycotic active substance is preferably a drug from the group of nystatin, ciclopirox or ciclopiroxolamine, or one from the group of azoles (imidazoles, triazoles, tetraazoles) such as clotrimazole, fluconazole, miconazole, itraconazole, tioconazole, voriconazole, bifonazole, econazole, isoconazole, fenticonazole, sertaconazole, ketoconazole, posaconazole, quilseconazole, oteseconazole (VT-1161), from Ibrexafungerp (SCY-078).

Medicaments according to the present invention have been developed primarily for the treatment of vaginosis and cystitis. The invention therefore relates to the use of the emulsions according to the invention in the topical treatment of infectious diseases, in particular for use in the topical treatment of urogenital infections. Preferably, the infectious disease is a microbial (especially a bacterial) urogenital infection, especially a microbial (especially a bacterial) urogenital infection of the woman. In a particularly preferred embodiment, the infectious disease is a mixed vaginal infection caused by *Candida albicans* and bacteria such as *Enterobacter, E. coli, Klebsiella pneumoniae, Gardnerella vaginalis,* or *Prevotella* spp. In another preferred embodiment, the infectious disease is an asymptomatic or symptomatic bacterial vaginosis or an asymptomatic or symptomatic dysbiosis of the glans penis and/or the male urethra.

Both acne and genetic hair loss are associated with the male sex hormone testosterone. In fact, the contribution of this hormone to the pathogenetic process consists primarily in the activation of sebaceous glands in the skin and hair follicles. The accumulated sebum is subsequently an ideal substrate for bacterial infection, especially with propionibacteria or with the fungi *Candida* and *Malassezia*. While *Malassezia* is mainly associated with *pityriasis versicolor, Propionibacterium acnes* is the main cause of acne. Both are involved in hair loss. The large amount of sebum that accumulates in the hair follicles is an ideal substrate for the formation of a biofilm. In principle, the same criteria apply to this biofilm as to biofilms that form in the vagina. In this case, too, the biofilm must first be broken up and its adhesion to the epithelium dissolved so that the anti-infective agent can subsequently exert its effect. Accordingly, according to the present invention, the emulsions are also very well suited for the treatment of skin diseases, especially *Pityriasis versicolor*, acne and hair loss. As the dermal applications can affect a considerably larger and much less defined area than vaginal infections, special emulsions may be preferred in these cases. In particular, shampoos are suitable for the treatment of hair loss, and acne creams, acne sticks or acne solutions are suitable for the treatment of acne.

The invention will be explained in greater detail hereinafter by means of the following examples, to which it is not, however, restricted.

EXAMPLES

Preparation of Basic Formulation A, General Preparation Instructions 1:

The components sorbitan monostearate, polysorbate 60, cetyl palmitate, 2-octyldodecanol and cetostearyl alcohol are melted at a temperature of 70-75° C. Clindamycin (and optionally clotrimazole) and then phenoxyethanol are added to the clear melt while stirring at a temperature of 60° C.-70° C. At the same time, diclofenac sodium is dissolved in purified water while heating. The aqueous solution is added to the oil phase while stirring and homogenised. Under slow cooling with further homogenisation of the w/o emulsion formed, a phase inversion takes place which results in a hydrophilic, homogeneous cream.

| Constituents of the emulsion | | |
|---|---|---|
| Clindamycin | 2.00 | 2.00 |
| Diclofenac Na | 0.20 | 0.30 |
| Sorbitan monostearate | 2.00 | 2.00 |
| Polysorbate 60 | 1.50 | 1.50 |
| Cetylpalmitate | 3.00 | 3.00 |
| 2-octyldodecanol | 13.50 | 13.50 |
| Cetostearyl alcohol | 10.00 | 10.00 |
| Phenoxyethanol | 1.00 | 1.00 |
| Purified water Ph. Eur. | 66.80 | 66.70 |
| | 100.00 | 100.00 |

Emulsions which Contain Phenoxyethanol as Antibacterial Agent

TABLE F1

| phenoxyethanol as antibacterial agent | |
|---|---|
| Composition of the emulsion | wt. % |
| Clotrimazole | 1 |
| Diclofenac Na | 0.4 |
| Sorbitan monostearate | 2 |
| Polysorbate 60 | 1.5 |
| Cetylpalmitate | 3 |
| 2-octyldodecanol | 13.5 |
| Cetylstearyl alcohol | 10 |
| Phenoxyethanol | 4 |
| Purified water Ph. Eur. | 64.6 |
| Total | 100 |

Case study: 24-year-old female patient (EH), almost constant complaints due to fungal infections for 3 years, intercourse hardly possible for years. For 1 week extreme complaints. Burning and itching in the introitus.

Gynaecological examination (Gyn.E.): Vulva and vaginal mucosa massively reddened, solid creamy greenish vaginal contents, secretion smear native: masses of leukocytes adhering to the epithelial cells and to masses of fungal hyphae, mixed flora, few lactobacilli, dirty background—lytic cells, intermediate flora.

Therapy: F1 over 2 weeks,
0-0-1 Hb applied vaginally, then F1 if required.

Check-up after 3 years: free of complaints since last therapy;

Gyn.E.: Mucosa bland, normal vaginal flora, lactobacilli flora.

Example: Emulsions Containing Dequalinium Chloride

TABLE F2

| Dequalinium chloride as antibacterial agent | |
|---|---|
| Composition of the emulsion | wt. % |
| Clotrimazole | 1 |
| Diclofenac Na | 0.3 |
| Sorbitan monostearate | 2 |
| Polysorbate 60 | 1.5 |
| Cetylpalmitate | 3 |
| 2-octyldodecanol | 13.5 |
| Cetostearyl alcohol | 10 |
| Phenoxyethanol | 1 |
| Dequalinium chloride | 0.4 |
| Purified water Ph. Eur. | 67.3 |
| Total | 100 |

Case study: 40-year-old female patient (AKS), almost monthly complaints due to fungal infections for years, in each case for about 1 week to 10 days, intercourse hardly possible for years. For 1 week additionally thin and malodorous vaginal secretion. Burning and itching in the introitus.

Gynaecological examination: Mucosa strongly reddened, secretion thin, slightly greenish. Secretion smear native: abundant biofilm plaques on thick fungal hyphae, leukocytes +++, hardly any lactobacilli, intermediate flora.

Therapy: F2 over 1 week, 0-0-1 Hb applied vaginally.

Check-up after 2 years: free of symptoms for 2 years, only occasionally very slight fungal infection, treated with residual F2;

Gyn.E.: Mucosa bland, lactobacilli flora

TABLE F3

| Dequalinium chloride as antibacterial agent | |
|---|---|
| Composition of the emulsion | wt. % |
| Clotrimazole | 1.00 |
| Diclofenac Na | 0.20 |
| Sorbitan monostearate | 2.00 |
| Polysorbate 60 | 1.50 |
| Cetylpalmitate | 3.00 |
| 2-octyldodecanol | 13.50 |
| Cetostearyl alcohol | 10.00 |
| Propylene glycol | 7.00 |
| Dequalinium chloride | 0.40 |
| Purified water Ph. Eur. | 61.40 |
| Total | 100.00 |

Case study: 31-year-old female patient (FJ), almost monthly premenstrual complaints for approx. 3 years, in each case for approx. 1 week to 10 days, due to recurrent fungal infections. For 1 week additionally thin and malodorous vaginal secretion. Burning and itching in the introitus.

Gyn.E: Mucosa slightly reddened, secretion thin, odour. secretion smear native: bacterial vaginosis (RG III), additionally fungal hyphae, abundant leucocytes.

Therapy: F3 over 1 week, 0-0-1 Hb applied vaginally.

Check-up after 4 months: subjectively no more complaints since therapy. Gyn.E: mucosa bland, secretion smear native: normal vaginal flora (RG I)

Example: Emulsions Containing Clindamycin

TABLE F4

| Composition of the emulsion | wt. % |
|---|---|
| Clindamycin | 2 |
| Diclofenac Na | 0.3 |
| Sorbitan monostearate | 2 |
| Polysorbate 60 | 1.5 |
| Cetylpalmitate | 3 |
| 2-octyldodecanol | 13.5 |
| Cetostearyl alcohol | 10 |
| Propylene glycol | 7 |
| Phenoxyethanol | 1 |
| Purified water Ph. Eur. | 59.70 |
| Total | 100 |

Case study: 31-year-old female patient (EK), bacterial vaginosis resistant to therapy for months, malodorous discharge, especially postmenstrual. In the microbial smear result plenty of *Gardnerella* and *Prevotella*.

Gyn.E: Mucosa strongly reddened, vaginal secretion thin and malodorous. Secretion smear native: plenty of clue cells, leucocytes +++, bacterial vaginosis (RG III)

Therapy: F4 over 1 week, 0-0-1 vaginally applied, then Hylaktiv Vagilact.

Check-up after 2 years: since above-mentioned therapy free of complaints, once very slight fungal infection; Gyn.E.: mucosa bland, normal lactobacilli flora (RG I)

Example: Emulsions Containing Phosphomycin-Trometamol

TABLE F5

| Composition of the emulsion | wt. % |
|---|---|
| Phosphomycin trometamol | 2 |
| Diclofenac Na | 0.4 |
| Sorbitan monostearate | 2 |
| Polysorbate 60 | 1.5 |
| Cetylpalmitate | 3 |
| 2-octyldodecanol | 13.5 |
| Cetylstearyl alcohol | 10 |
| Phenoxyethanol | 1 |
| Purified water Ph. Eur. | 66.6 |
| Total | 100 |

Case study: 69-year-old female patient (ET), recurrent urinary tract infections for about 2 years, repeatedly treated with Ciproxin. For 2 weeks increased urge to urinate and burning in the introitus.

Gyn.E: Pressure pain over bladder; mucosa atrophic, bleeds on contact, cervix atrophic, soldered, opened with cervix brush, secretion: atrophy, aerobic mixed flora (RGIII), abundant leukocytes.

Therapy: F5 over 1 week, 0-0-1 Hb vaginally applied, additionally Ovestin.

Control examination after 2 weeks: subjectively no more complaints since therapy.

Gyn.E: mucosa bland, no pressure pain over bladder and urethra; secretion smear native: beginning of normal vaginal flora (RG I), no leukocytes.

TABLE F6

| Composition of the emulsion | wt. % |
|---|---|
| Phosphomycin trometamol | 2 |
| Clotrimazole | 1 |
| Diclofenac Na | 0.3 |
| Sorbitan monostearate | 2 |
| Polysorbate 60 | 1.5 |
| Cetylpalmitate | 3 |
| 2-octyldodecanol | 13.5 |
| Cetostearyl alcohol | 10 |
| Propylene glycol | 7 |
| Phenoxyethanol | 1 |
| Purified water Ph. Eur. | 58.7 |
| Total | 100 |

Case study: 36-year-old female patient (CS), 2 years ago first UTI after vacation in Thailand with macrohaematuria and long-lasting burning sensation, for 2 months again pain in the lower abdomen and UTI (again after vacation in Thailand), burning sensation again and again especially after urination, for 2 weeks increased urge to urinate again, after AB-treatment (1 week) no improvement of bladder problems but now additionally itching and burning sensation in the introitus.

Gynaecological examination: pressure pain over the bladder; vaginal mucosa rather inconspicuous, pronounced cervicitis with bloody erosion around the cervix measuring about 1 cm, secretion/native preparation: bacterial vaginosis, masses of leukocytes, these covered with bacteria, isolated lactobacilli, hyphae ++. Microbiol. smear—secretion culture: masses of *E. coli*.

Therapy: F6 over 10 days, 0-0-1 vaginally applied, additionally 2 Btl Monuril at intervals of 3 days.

Check-up after 4 weeks: subjectively no more complaints since therapy.

Gyn.E.: mucosa bland, no pressure pain over bladder and urethra; secretion smear native: normal vaginal flora (RG I), no leukocytes.

TABLE F7

| Composition of the emulsion | wt. % |
|---|---|
| Phosphomycin trometamol | 2 |
| Diclofenac Na | 0.3 |
| Sorbitan monostearate | 2 |
| Polysorbate 60 | 1.5 |
| Cetylpalmitate | 3 |
| 2-octyldodecanol | 13.5 |
| Cetostearyl alcohol | 10 |
| Propylene glycol | 7 |
| Phenoxyethanol | 1 |
| Purified water Ph. Eur. | 59.7 |
| Total | 100 |

Example: Influence of the Aqueous Phase/Oil Weight Ratio on the Clinical Efficacy of the NSAID Surprisingly, changes in viscosity show clear influences on clinical efficacy even with a small range of variation. The stated examples were prepared according to general preparation instructions 1 by varying the content of fatty components and the water content.

An increase in the water content and thus a decrease in viscosity leads to local irritation and reduced clinical efficacy through increased release and increased wetting of the mucosas.

TABLE

Influence of the aqueous phase/oil weight ratio on the clinical efficacy

| Phase | Fat component/ viscosity reduced | | Basic formulations | | Fat component/ viscosity increased | |
|---|---|---|---|---|---|---|
| Clotrimazole (oil) | 1 | 1.0 | 1.0 | 1.0 | 1.0 | 1.0 |
| Diclofenac Na (water) | 0.3 | 0.3 | 0.3 | 0.3 | 0.3 | 0.3 |
| Sorbitan monostearate (—) | 2.0 | 2.0 | 2.0 | 2.0 | 2.0 | 2.0 |
| Polysorbate 60 (—) | 1.5 | 1.5 | 1.5 | 1.5 | 1.5 | 1.5 |
| Cetylpalmitate (oil) | 3.0 | 3.0 | 3.0 | 3.0 | 3.0 | 3.0 |
| 2-octyldodecanol (oil) | 13.5 | 13.5 | 13.5 | 13.5 | 13.5 | 14.5 |
| Cetylstearyl alcohol (oil) | 7.5 | 5 | 10 | 10 | 14 | 16 |
| Benzyl alcohol (oil) | 1.0 | 1.0 | 1.0 | | 1.0 | 1.0 |
| Phenoxyethanol (oil) | | | | 1.0 | | |
| Propylene glycol (water) | | | | 7 | | |
| Water (water) | 70.2 | 72.7 | 67.75 | 60.7 | 63.7 | 60.7 |
| Total | 100 | 100 | 100 | 100 | 100 | 100 |
| Clinical efficacy | irritating | irritating | conforms | conforms | reduced | reduced |
| Water phase total | 70.5 | 73.0 | 68.0 | 68.0 | 64.0 | 61.0 |

TABLE-continued

Influence of the aqueous phase/oil weight ratio on the clinical efficacy

| Phase | Fat component/ viscosity reduced | | Basic formulations | | Fat component/ viscosity increased | |
|---|---|---|---|---|---|---|
| Fat phase total | 26 | 23.5 | 28.5 | 28.5 | 32.5 | 35.5 |
| aqueous phase/fat | 2.7 | 3.1 | 2.4 | 2.4 | 2.0 | 1.7 |

To calculate the weight ratio of the water phase to the oil phase, the individual proportions of the water and oil phases are added together as shown in the table. Since emulsifiers, for example sorbitan monostearate and polysorbate 60, are located at the interfaces between the two phases, they are not assigned to either the water or the oil phase.

If the ratio of the aqueous phase to the oil phase of the concentrated emulsion (i.e. the intermediate product of components A, B, J, C, E, G, H and half of K) of example 2 of WO 02/0768648 A2 is calculated, a ratio of 3.1 is obtained (oil phase:terbinafine, butylhydroxytoluene, benzyl alcohol, isopropyl myristate, total 11.52 g/100 g; water phase: diclofenac sodium and water, total 35.94 g/100 g; ratio 3.1). Such an emulsion therefore has a water-to-oil ratio outside the scope of the invention and would therefore not be suitable in the context of the present invention.

Alternatively, the weight ratio of the water phase to the oil phase could be calculated without including the substances dissolved in the phases (clotrimazole, diclofenac Na, benzyl alcohol, cetylstearyl alcohol). With this method of calculation, only water and propylene glycol would be attributed to the water phase in Table 3, and cetyl palmitate, 2-octyldodecanol and cetylstearyl alcohol to the oil phase. The water-to-oil ratios 2.7, 3.1, 2.4, 2.4, 2.0, 1.7 given in Table 3 would correspond to the values 2.9, 3.4, 2.6, 2.6, 2.1, 1.8 according to this calculation method. The range according to the invention of 2.0 to 2.7 would correspond to a range of 2.1 to 2.9 according to this calculation method.

In the context of the present invention, however, the calculation of the weight ratio of the water phase to the oil phase shall be carried out as shown in Table 3, i.e. including the substances dissolved in the phases.

Further examples of the influence of the aqueous phase/oil weight ratio on clinical efficacy:

Example: Influence of the pH Value on the Clinical Efficacy of the NSAID

Using emulsions with clotrimazole and NSAIDs, the influence of pH value on the clinical efficacy of the NSAID was investigated. Emulsions with different concentrations of diclofenac Na were prepared and examined for their clinical efficacy.

TABLE

Dependence of clinical efficacy on the concentration of the NSAID

| | Conc. wt. % | Conc. wt. % | Conc. wt. % | Conc. wt. % |
|---|---|---|---|---|
| Clotrimazole | 1 | 1 | 1 | 1 |
| Diclofenac Na | 0.1 | 0.25 | 0.5 | 0.75 |
| Sorbitan monostearate | 2 | 2 | 2 | 2 |
| Polysorbate 60 | 1.5 | 1.5 | 1.5 | 1.5 |
| Cetylpalmitate | 3 | 3 | 3 | 3 |
| 2-octyldodecanol | 13.5 | 13.5 | 13.5 | 13.5 |
| Cetylstearyl alcohol | 10 | 10 | 10 | 10 |
| Benzyl alcohol | 1 | 1 | 1 | 1 |
| Purified water Ph. Eur. | 67.9 | 67.75 | 67.5 | 67.25 |
| Total | 100 | 100 | 100 | 100 |
| Ph | 7.6 | 7.8 | 8.1 | 8.1 |
| Clin. efficacy | slightly reduced | conforms | conforms, slightly irritating | irritating to the mucosa |

The combined use of clotrimazole and NSAIDs changes both microbiological and chemical stability [Lit. Pharmacopoeia] compared to a comparable clotrimazole formulation due to the pH shifts in the emulsion system.

| | | Fat component/ viscosity reduced | | Basic formulations | | | Fat component/ viscosity increased | |
|---|---|---|---|---|---|---|---|---|
| Clotrimazole | oil | 1.00 | 1.00 | 1 | 1 | 1 | 1.00 | 1.00 |
| Diclofenac Na | water | 0.30 | 0.30 | 0.25 | 0.3 | 0.4 | 0.30 | 0.30 |
| Sorbitan monostearate | | 2.00 | 2.00 | 2 | 2 | 2 | 2.00 | 2.00 |
| Polysorbate 60 | | 1.50 | 1.50 | 1.5 | 1.5 | 1.5 | 1.50 | 1.50 |
| Cetylpalmitate | oil | 3.00 | 3.00 | 3 | 3 | 3 | 3.00 | 3.00 |
| 2-octyldodecanol | oil | 13.50 | 13.50 | 13.5 | 13.5 | 13.5 | 13.50 | 14.50 |
| Cetylstearyl alcohol | oil | 7.50 | 5.00 | 10 | 10 | 10 | 14.00 | 16.00 |
| Benzyl alcohol | oil | 1.00 | 1.00 | 1 | | | 1.00 | 1.00 |
| Phenoxyethanol | oil | | | | 1 | 4 | | |
| Propylene glycol | water | | | | 7 | | | |
| Purified water Ph. Eur. | water | 70.20 | 72.70 | 67.75 | 60.7 | 64.6 | 63.70 | 60.70 |
| Total | | 100.00 | 100.00 | 100.00 | 100.00 | 100.00 | 100.00 | 100.00 |
| Clinical efficacy | | irritating | irritating | conforms | conforms | conforms | reduced | reduced |
| aqueous phase/fat | | 2.7 | 3.1 | 2.4 | 2.4 | 2.1 | 2.0 | 1.7 |
| Water phase | | 70.50 | 73.00 | 68.00 | 68.00 | 65.00 | 64.00 | 61.00 |
| Fat phase | | 26.00 | 23.50 | 28.50 | 28.50 | 31.50 | 32.50 | 35.50 |

TABLE

Variants with different preservatives

| Composition | wt. % | wt. % | wt. % | wt. % | wt. % |
|---|---|---|---|---|---|
| Clotrimazole | 1 | 1 | 1 | 1 | 1 |
| Diclofenac Na | 0.4 | 0.3 | 0.3 | 0.25 | 0.25 |
| Sorbitan monostearate | 2 | 2 | 2 | 2 | 2 |
| Polysorbate 60 | 1.5 | 1.5 | 1.5 | 1.5 | 1.5 |
| Cetylpalmitate | 3 | 3 | 3 | 3 | 3 |
| 2-octyldodecanol | 13.5 | 13.5 | 13.5 | 13.5 | 13.5 |
| Cetylstearyl alcohol | 10 | 10 | 10 | 10 | 10 |
| Propylene glycol | | 7 | 5 | | |
| Phenoxyethanol | 4 | 1 | 1 | 1 | |
| Bronopol | | | | 0.1 | |
| Sorbic acid | | | | | 0.2 |
| Buffer solution | | | | 0.2201 | 0.0874 |
| Purified water Ph.Eur. | 64.6 | 60.7 | 62.7 | 67.4299 | 68.4626 |
| Total | 100 | 100 | 100 | 100 | 100 |
| Ph | 7.9 | 7.6 | 7.9 | 7.5 | 5.6 |
| Clin. efficacy | conforms | conforms | conforms | conforms | reduced |
| Microbiol. stability | conforms | conforms | conforms | conforms | conforms |

Example: Shampoo for the Treatment of Fungal Hair Loss

TABLE F8

| Composition of the emulsion | wt. % |
|---|---|
| Ketoconazole | 2 |
| Diclofenac Na | 0.3 |
| Ammonium lauryl sulfate | 15.00 |
| Lauramide | 4.00 |
| Sodium chloride | 1.00 |
| Farnesol | 1 |
| Disodium EDTA | 0.2 |
| Methylparaben | 0.08 |
| Propylparaben | 0.05 |
| Purified water Ph. Eur. | 76.37 |
| | 100 |

Structural Formula of Ibrexafungerp (SCY-078).

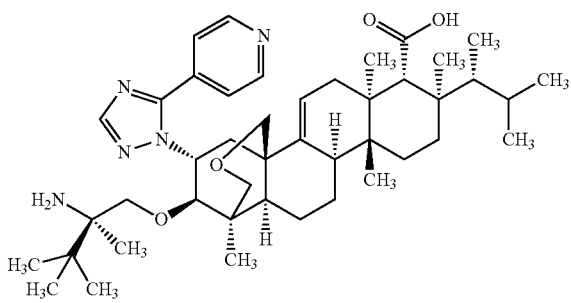

Structural Formula of Oteseconazole (VT-1161).

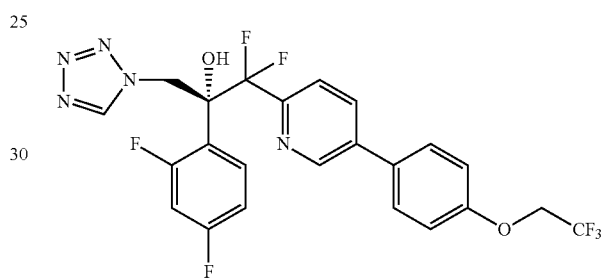

Accordingly, the invention relates to the following preferred embodiments:

1. An emulsion for the topical treatment of dermal infections and mucosal infections, in particular of urogenital infectious diseases, characterised in that an antimicrobial active substance and an anti-adhesive active substance, preferably an NSAID, are used in combination.

2. An emulsion according to embodiment 1, which additionally contains an antimycotic active substance.

3. An emulsion according to embodiment 1 or 2, preferably in the form of a salve or a cream, with an aqueous phase and an oil phase, containing an antimicrobial active substance and an NSAID, characterised in that (a) the NSAID in the aqueous phase is in a concentration range that corresponds to half to a tenth of the standard concentration used for these active substances in approved dermal formulations, in that (b) the weight ratio of the water phase to the oil phase in this emulsion is between the values 2.0 and 2.7, and in that (c) the pH value of the emulsion is not less than the value 6.5 and not more than 8.5, preferably in the range 7.0 to 8, preferably for the treatment of urogenital infectious diseases, in particular for use in the topical treatment of vaginal infections and female cystitis, and for local partner treatment (glans penis, initial third of the urethra).

4. An emulsion according to embodiment 1 or 2, preferably in the form of a salve, cream, shampoo, solution or stick, with an aqueous phase and an oil phase, containing an antimicrobial active substance and an NSAID, characterised in that (a) the NSAID in the aqueous phase is in a concentration range which, in the event of cutaneous application, corresponds to at most the standard concentration, and in the event of application to mucosas corresponds to half to a tenth of the standard concentration for these active substances, and in that (b) the pH value of the emulsion is not less than the value 5.5 and not more than 8.5, preferably for the topical treatment of dermal infections, in particular for use in the topical treatment of acne, hair loss, *Pityriasis versicolor* and atopic dermatitis.

5. An emulsion according to one of embodiments 1 to 4, characterised in that the NSAID is diclofenac, bufexamac, ibuprofen, dexibuprofen, flurbiprofen, ketoprofen, piroxicam, meloxicam, lornoxicam, flufenamic acid, mefenamic acid, indometacin or naproxen.

6. An emulsion according to one of embodiments 1 to 5, characterised in that the antimicrobial active substance is an antibiotic.

7. An emulsion according to embodiment 6, characterised in that the antibiotic is phosphomycin, clindamycin, metronidazole, nitrofurantoin, nitrofurazone, nitrofurantoin, nifuratel, nifuroxacin, nitroxolin, trimethoprim, sulfadiazine, or cotrimoxazole.

8. An emulsion according to one of embodiments 1 to 7, characterised in that the antimicrobial active substance is an antiseptic.

9. An emulsion according to embodiment 8, characterised in that the antiseptic is selected from the group consisting of: benzalkonium chloride, preferably in a concentration of at least 0.2 weight percent; dequalinium chloride, preferably in a concentration of at least 0.2 weight percent; and phenoxyethanol, preferably in a concentration of at least 2 weight percent.

10. An emulsion according to one of embodiments 2 to 9, characterised in that the antimycotic active substance is nystatin, ciclopirox or ciclopiroxolamine, or an antimycotic from the group of azoles, preferably clotrimazole, fluconazole, miconazole, itraconazole, tioconazole, voriconazole, bifonazole, econazole, isoconazole, fenticonazole, sertaconazole, ketoconazole, posaconazole, quilseconazole, oteseconazole (VT-1161) or ibrexafungerp (SCY-078).

11. An emulsion according to one of embodiments 1 to 10, characterised in that the NSAID is diclofenac and this is contained in a concentration range of 0.2-0.4 weight percent of the emulsion.

12. An emulsion according to one of embodiments 1 to 11, characterised in that it further contains an odorous substance, preferably a terpene, in particular farnesol.

13. An emulsion according to one of embodiments 1 to 12 for use in the topical treatment of infectious diseases, in particular for use in the topical treatment of dermal and urogenital infectious diseases.

14. An emulsion for use according to embodiment 13, characterised in that the infectious disease is a mucosal infection, in particular a urogenital infection.

15. Emulsion for use according to embodiment 13 or 14, characterised in that the infectious disease is a microbial urogenital infection, in particular a microbial urogenital infection of the woman.

16. Emulsion for use according to embodiment 15, characterised in that the microbial urogenital infection is a bacterial urogenital infection.

17. Emulsion for use according to one of embodiments 13 to 16, characterised in that the infectious disease is a mixed vaginal infection by *Candida albicans* and bacteria such as *Enterobacter, E. coli, Klebsiella pneumoniae, Gardnerella vaginalis*, or *Prevotella* spp.

18. Emulsion for use according to one of embodiments 13 to 17, characterised in that the infectious disease is an asymptomatic or symptomatic bacterial vaginosis or an asymptomatic or symptomatic dysbiosis of the glans penis and/or the male urethra.

19. Emulsion for use according to one of embodiments 13 to 18, characterised in that the infectious disease is a chronic infectious disease.

20. Emulsion according to one of embodiments 1 to 12 for use in the treatment of acne.

21. Emulsion according to embodiment 20, characterised in that the emulsion is processed into an acne stick or an acne solution.

22. Emulsion according to one of embodiments 1 to 12 for use in the treatment of dermal fungal infections, preferably *Candida* mycoses and *Malassezia* mycoses.

23. Emulsion, preferably shampoos, according to one of embodiments 1 to 12 for use in the treatment of hair loss.

24. A process for preparing an emulsion according to one of embodiments 1 to 12, characterised in that, when preparing the emulsion, the NSAID is introduced via the aqueous phase.

25. A process for preparing an emulsion according to one of embodiments 1 to 12, characterised in that the NSAID is introduced as a finely crystalline or micronised salt into the emulsion containing the antimycotic.

The invention claimed is:

1. An emulsion, comprising:
an antimicrobial active substance selected from the group consisting of an antibiotic and an antiseptic, and
an NSAID,
wherein (a) the NSAID is diclofenac in a concentration of 0.1 to 0.5 weight percent, indomethacin in a concentration of 0.1 to 0.4 weight percent, naproxen in a concentration of 1 to 5 weight percent, ibuprofen in a concentration of 0.5 to 2.5 weight percent, dexibuprofen in a concentration of 0.25 to 1.25 weight percent, ketoprofen in a concentration of 0.25 to 1.25 weight percent, mefenamic acid in a concentration of 0.5 to 4 weight percent, or lornoxicam in a concentration of 0.02 to 0.04 weight percent,
the NSAID is present in salt form; while (b) a weight ratio of an aqueous phase to an oil phase in the emulsion is between 2.0 and 2.7, and (c) a pH value of the emulsion is not less than 6.5 and not more than 8.5, and
the emulsion is suitable for topical treatment of a dermal infection or a mucosal infection.

2. The emulsion according to claim 1, further comprises an antimycotic active substance.

3. The emulsion according to claim 1, wherein the emulsion is in the form of a salve, cream, shampoo, solution or stick, for the topical treatment of dermal infections.

4. The emulsion according to claim 1, wherein the antimicrobial active substance is an antibiotic.

5. The emulsion according to claim 4, wherein the antibiotic is phosphomycin, clindamycin, metronidazole, nitrofurantoin, nitrofurazone, nitrofurantoin, nifuratel, nifuroxacin, nitroxolin, trimethoprim, sulfadiazine, or cotrimoxazole.

6. The emulsion according to claim 1, wherein the antimicrobial active substance is an antiseptic.

7. The emulsion according to claim 6, wherein the antiseptic is selected from the group consisting of benzalkonium chloride; dequalinium chloride; and phenoxyethanol.

8. The emulsion according to claim 2, wherein the antimycotic active substance is nystatin, ciclopirox, ciclopiroxolamine, or an antimycotic selected from the group consisting of clotrimazole, fluconazole, miconazole, itraconazole, tioconazole, voriconazole, bifonazole, econazole, isoconazole, fenticonazole, sertaconazole, ketoconazole, nosaconazole, quilseconazole, and oteseconazole.

9. The emulsion according to claim 1, wherein the NSAID is diclofenac and is contained in a concentration range of 0.2-0.4 weight percent of the emulsion.

10. The emulsion according to claim 1, further comprising:
   an odorous substance.

11. A method for topical treatment of infectious disease, the method comprising:
   applying the emulsion according to claim 1 to a subject in need thereof.

12. The method according to claim 11, wherein the infectious disease is a mucosal infection.

13. The method according to claim 11, wherein the infectious disease is a microbial urogenital infection.

14. The method according to claim 13, wherein the microbial urogenital infection is a bacterial urogenital infection.

15. The method according to claim 11, wherein the infectious disease is a mixed vaginal infection by *Candida albicans Candida albicans* and bacteria.

16. The method according to claim 11, wherein the infectious disease is an asymptomatic or symptomatic bacterial vaginosis or an asymptomatic or symptomatic dysbiosis of glans penis and/or male urethra.

17. The method according to claim 11, wherein the infectious disease is a chronic infectious disease.

18. The method according to claim 11, wherein the infectious disease is a dermal fungal infection.

19. The method according to claim 11, wherein the infectious disease is acne.

20. The method according to claim 19, wherein the emulsion is processed into an acne stick.

21. The method according to claim 11, wherein the method is for topical treatment of female cystitis, and for local partner treatment (glans penis, initial third of the urethra).

22. The method according to claim 11, wherein the method is for treatment of hair loss.

23. The method according to claim 11, wherein the method is for topical treatment of atopic dermatitis,
   wherein the emulsion is in the form of a salve, cream, shampoo, solution or stick.

24. A process for preparing the emulsion according to claim 1, the process comprising:
   introducing the NSAID into the aqueous phase.

25. A process for preparing the emulsion according to claim 2, the process comprising:
   introducing the NSAID as a finely crystalline or micronised salt into an emulsion comprising the antimycotic.

* * * * *